(12) United States Patent
Batistoni et al.

(10) Patent No.: US 8,417,002 B2
(45) Date of Patent: Apr. 9, 2013

(54) METHOD FOR ANALYZING IMAGE DATA RELATING TO AGGLUTINATION ASSAYS

(75) Inventors: Julio Batistoni, Montevideo (UY); Juan Andres Abin, Montevideo (UY); Alvaro Pardo, Montevideo (UY)

(73) Assignee: Laboratorios Celsius S.A., Montevideo (UY)

( * ) Notice: Subject to any disclaimer, the term of this patent is extended or adjusted under 35 U.S.C. 154(b) by 0 days.

(21) Appl. No.: 12/516,716

(22) PCT Filed: Nov. 29, 2006

(86) PCT No.: PCT/IB2006/004033
§ 371 (c)(1),
(2), (4) Date: Aug. 13, 2009

(87) PCT Pub. No.: WO2008/065474
PCT Pub. Date: Jun. 5, 2008

(65) Prior Publication Data
US 2009/0324036 A1 Dec. 31, 2009

(51) Int. Cl.
*G06K 9/00* (2006.01)

(52) U.S. Cl.
USPC ........................................................ 382/128

(58) Field of Classification Search ................ 382/128, 382/129, 133, 134; 128/920; 356/39; 435/7.1; 348/80
See application file for complete search history.

(56) References Cited

U.S. PATENT DOCUMENTS

| | | | | |
|---|---|---|---|---|
| 4,680,274 A | * | 7/1987 | Sakai et al. | 436/512 |
| 4,794,450 A | * | 12/1988 | Saito et al. | 348/61 |
| 5,541,417 A | * | 7/1996 | Xiong et al. | 250/559.05 |
| 5,628,963 A | * | 5/1997 | Meller et al. | 422/73 |
| 5,768,407 A | * | 6/1998 | Shen et al. | 382/133 |
| 5,783,446 A | * | 7/1998 | Saul et al. | 436/45 |
| 6,249,593 B1 | | 6/2001 | Chu et al. | |
| 2002/0168784 A1 | * | 11/2002 | Sundrehagen et al. | 436/536 |
| 2006/0282221 A1 | * | 12/2006 | Shah et al. | 702/19 |
| 2007/0160978 A1 | * | 7/2007 | Escarguel | 435/5 |
| 2008/0003599 A1 | * | 1/2008 | Dary et al. | 435/6 |

FOREIGN PATENT DOCUMENTS

| | | |
|---|---|---|
| EP | 0 637 744 A1 | 2/1995 |
| EP | 0 902 394 A1 | 3/1999 |
| WO | 98/32004 A1 | 7/1998 |
| WO | 00/05571 A1 | 2/2000 |

OTHER PUBLICATIONS

Bloem et al Fully automatic determination of soil bacterium numbers, cell volumes, and frequencies of dividing cells by confocal lase3r scanning microscopy and image analysis', Applied and environmental Microbiology, p. 926-936, Mar, 1995.*

* cited by examiner

*Primary Examiner* — Claire X Wang
*Assistant Examiner* — Shervin Nakhjavan
(74) *Attorney, Agent, or Firm* — Sughrue Mion, PLLC

(57) ABSTRACT

A method for analyzing a digital image containing the result of an agglutination assay to generate a quantitative result value representative of the degree of agglutination of the sample is provided. The method for analyzing the digital image includes: applying a filter to extract a component of the image or portion of a spectrum where a signal to noise ratio between agglutinated and background is maximized; extracting a set of features that characterize the agglutination pattern, obtaining a quantification function which maps measured features to the actual concentration of the sample and computing a quantitative result for each sample in the assay.

10 Claims, 11 Drawing Sheets

| Workman | Latex (Batch Number) | Image Number | T°C | Day |
|---|---|---|---|---|
| A | 1 | I | 24 | 1 |
| A | 2 | II | 24 | 1 |
| B | 1 | III | 24 | 1 |
| A | 1 | IV | 25,5 | 2 |
| A | 2 | V | 25,5 | 2 |
| B | 1 | VI | 25,5 | 2 |
| A | 1 | VII | 23,5 | 3 |

FIG. 5

| Image Number | Negative Control | IU/ml | | | | | | | | | | |
|---|---|---|---|---|---|---|---|---|---|---|---|---|
| | | 4 | 6 | 8 | 10 | 12 | 14 | 16 | 18 | 20 | 22 | 24 |
| I | 3,981 | 3,768 | 4,348 | 5,732 | 5,516 | 7,039 | 7,338 | 8,121 | 8,883 | 9,445 | 9,409 | 10,049 |
| II | 3,728 | 3,885 | 4,300 | 5,372 | 6,725 | 6,476 | 7,226 | 6,965 | 7,643 | 7,975 | 8,436 | 8,796 |
| III | 4,187 | 4,145 | 4,424 | 5,481 | 6,769 | 7,242 | 7,252 | 7,994 | 8,545 | 9,114 | 9,168 | 9,835 |
| IV | 4,160 | 4,270 | 4,323 | 5,928 | 7,400 | 6,941 | 8,028 | 7,780 | 8,361 | 8,424 | 9,076 | 9,192 |
| V | 3,911 | 4,086 | 4,243 | 5,128 | 6,378 | 6,600 | 7,135 | 7,540 | 7,725 | 8,377 | 8,329 | 8,735 |
| VI | 3,866 | 4,240 | 4,018 | 4,473 | 5,780 | 6,536 | 6,987 | 7,641 | 7,563 | 8,706 | 8,116 | 8,812 |
| VII | 3,730 | 3,641 | 4,015 | 4,726 | 6,190 | 6,434 | 7,463 | 7,517 | 7,988 | 8,075 | 8,674 | 8,900 |

FIG. 6

| Dil. | Ref IU/ml well | Mean | Est. IU/ml | IU/ml | Mean IU/ml | Est. |
|---|---|---|---|---|---|---|
| ctrl- | 0 | 4,060 | 0 | | | |
| 1/8 | 2.5 | 3,982 | | | | |
| ¼ | 5 | 5,332 | 8,059 | 32,236 | | |
| ½ | 10 | 7,136 | 13,493 | 26,987 | | |
| 1 | 20 | 7,918 | – | | | |

FIG. 7

| dil. | Ref IU/ml well | Mean | IU/ml | Est. IU/ml | Mean Est. IU/ml |
|---|---|---|---|---|---|
| ctrl- | 0 | 3,787 | 0 | | |
| 1/64 | 5 | 7,003 | 12,824 | 410,366 | |
| 1/32 | 10 | 8,934 | 22,539 | 360,619 | |
| 1/16 | 20 | 10,563 | | | |
| 1 | 320 | 4,082 | --- | | |

FIG. 8

| dil. | Ref IU/ml well | Mean | Est. IU/ml | IU/ml | Mean IU/ml | Est. IU/ml |
|---|---|---|---|---|---|---|
| ctrl- | 0 | 4,082 | 0 | | | |
| 1/16 | 5 | 4,008 | | | | |
| 1/8 | 10 | 5,924 | 9,171 | 73,367 | | |
| ¼ | 20 | 8,572 | 20,718 | 82,871 | | |
| 1 | 80 | 11,593 | | | | |

FIG. 9

|  | Sample column 1 ||| Sample column 2 |||| Sample column 3 |||| Sample column 4 ||||
| --- | --- | --- | --- | --- | --- | --- | --- | --- | --- | --- | --- | --- | --- | --- | --- |
|  | Digital Result | Expert result | Expert Score | Digital Result | Digital Score | Expert result | Expert Score | Digital Result | Digital Score | Expert result | Expert Score | Digital Result | Digital Score | Expert result | Expert Score |
| Anti-B | Neg. | Neg. |  | Neg. |  | Neg. |  | Neg. |  | Neg. |  | Neg. |  | Neg. |  |
| Anti-A | Neg. | Neg. |  | Pos. | 3 | Pos. | 3 | Neg. |  | Neg. |  | Neg. |  | Neg. |  |
| Anti-AB | Neg. | Neg. |  | Pos. | 3 | Pos. | 3 | Neg. |  | Neg. |  | Neg. |  | Neg. |  |
| Alfa | Pos. | Pos. | [1] | Neg. |  | Neg. |  | Pos. | [1] | Pos. |  | Pos. | 2 | Pos. | 2 |
| Beta | Pos. | Pos. | [2] | Pos. | [3] | Pos. | [4] | Pos. | [2] | Pos. |  | Pos. | [2] | Pos. | [3] |
| Anti-D | Pos. | Pos. | [4] | Pos. | [3] | Pos. | [4] | Pos. | 3 | Pos. | 3 | Neg. |  | Neg. |  |
| Group | O+ | O+ |  | A+ | | A+ |  | O+ |  | O+ |  | O- |  | O- |  |

FIG. 10

|  | | \multicolumn{5}{c}{Classification} |
| --- | --- | --- | --- | --- | --- | --- |
| | | 0 | 1 | 2 | 3 | 4 |
| Ground truth | 0 | 0 | 0 | 0 | 0 | 0 |
| | 1 | ,17 | 1,43 | 2,70 | ,35 | ,35 |
| | 2 | ,00 | 8,10 | 9,05 | 0,95 | ,90 |
| | 3 | ,00 | ,00 | 8,33 | 8,33 | 3,33 |
| | 4 | ,00 | ,00 | ,00 | 9,61 | 0,39 |

FIG. 11

METHOD FOR ANALYZING IMAGE DATA RELATING TO AGGLUTINATION ASSAYS

BACKGROUND OF THE INVENTION

1. Field of the Invention

The present invention relates generally to a method for automatic analysis of agglutination assays and more specifically, provides a fast, simple and automatic diagnostic system which does not require expensive equipment and enables registration of an agglutination assay and its result for later use. Furthermore, the system is suitable for screening and batch processing multiple samples.

2. Description of the Related Art

Agglutination reactions are valuable analytical tools that can be applied to many reaction systems in which multivalent binding between reactants is possible. A particle agglutination immunoassay is advantageous in that it requires only the mixing of a sample to be tested with a suspension of insoluble carrier particles (e.g., latex) sensitized with an antibody or an antigen. Typical examples are immunoassays which generally involve:

a) mixing a sample containing an antibody, with an antigen (corresponding to the antibody on the sample) and observing immunocomplex formation;

b) mixing a sample containing an antigen carrying at least two antigenic functions (bivalent or multivalent antigen) with the corresponding antibody and observing immunocomplex formation;

c) mixing monoclonal antibodies with a sample containing at least two different monovalent antigens and observing immunocomplex formation;

d) for any of the reactions mentioned above, coupling the antigen or antibody to particles, such as latex particles, colloids, etc.; and observing immunoagglutinate formation.

e) in the case of rapid plasma reagin ("RPR") type reactions (e.g., for syphilis serodiagnostic), adding carbon as a visualizing agent and observing flocculation reactions;

f) for any of the reactions mentioned above, applying the above steps to antigens present on cell surfaces in which case the number of antigens per physical unit is normally a hundred or more, and in which case such cells may be agglutinated by monoclonal antibodies even if each antigen molecule is monovalent.

Such reactions are typically observed on the surface of a solid substrate such as a glass or plastic plate, or on the well of a microtitre plate. The solid surface is preferably colored to contrast with the color of the agglutinate.

The formation of visible agglutinates depends on the ratio of antigen/antibody. If a constant amount of antibody is mixed with increasing amounts of antigen three situations can be identified:

A pro-zone phenomenon, characterized by the presence of excess antibody in the test system and which is further characterized by non-occurrence of any visible phase reaction due to the inhibition of agglutinate formation by the excess antibody.

An equivalence zone characterized by the presence of antigen and antibody in optimum proportions and which is further characterized by enhanced agglutinate formation and visible phase reactions.

Post-zone Phenomenon characterized by the presence of excess antigen in the test system and which is further characterized by the nonoccurrence of visible reaction.

Pro-zone and Post-zone phenomena may be corrected by making serial dilutions of serum, thereby reducing the concentration of antigen or antibody in the test system, and optimizing the concentrations of antigen and antibody.

Agglutination reactions may also be performed with any set of molecules which bind to each other, provided that each of the reactants has at least two binding sites, or is coupled to a particle or otherwise linked together so that two or more binding sites per physical unit is created. Examples of systems other than antibodies/antigens that may form agglutinates are (poly)carbohydrates/lectins, biotin or biotinylated compounds/avidin or streptavidin, corresponding sequences of nucleic acids, any protein receptor and its corresponding ligand etc.

It can be appreciated that agglutination assays have been in use for years. Today, many agglutination assays are available to physicians for diagnosing various diseases, and an increasing number of such assays do not require that the patient's sample (e.g. blood, urine, saliva, stool) be sent to a diagnostic laboratory for analysis. Such in-office assays enable results to be obtained quickly and entered it to the patient's computer record. Test results can also be available for physicians in the emergency room.

Agglutination-based products for detection and quantification of analytes have been produced for a wide range of analytes. Very early on in the field, products were developed for the detection of human chorionic gonadotropic hormone (HCG) in urine, for the diagnosis of pregnancy. Two different principles were used: 1. products were made with antibodies on a particle surface, which gave agglutination in the presence of the analyte; and 2. products were made with antigen on the surface of the particles, and a reagent containing antibodies was added together with the test sample. In this second variant, agglutination took place in the absence or at low concentration of the analyte as a higher concentration of the analyte complexed with the antibodies and hindered the agglutination.

Furthermore, agglutination reagents for testing for drugs, including prescription drugs and most illegal drugs, and many non-proteinaceous hormones, such as testosterone, progesterone, oestriol, have been made.

The application of agglutination reactions is not confined to human or veterinary diagnostics, they function as great tools in other fields as well, including the agricultural industry, for detection of plant diseases (virus, bacteria and fungi) and industries which require monitoring of processes (e.g., the various food industries and the like).

It should be noted, however, that the examples given above are not considered to be a complete listing of the applications of agglutination assays and many other applications are possible.

Typical protein analytes for agglutination technology include C-reactive protein (CRP), transferrin, albumin, prealbumin, haptoglobin, immunoglobulin G, M, A and E, apolipoproteins, lipoproteins, ferritin, thyroid stimulation hormone (TSH) and other proteinaceous hormones, coagulation factors, plasminogen, plasmin, fibrinogen, fibrin split products, tissue plasminogen activator (TPA), betamicrogobulins, prostate-specific antigen (PSA), collagen, cancer markers (e.g. CEA andalphafoetoprotein), and several enzymes and markers for cell damage (e.g. myoglobin and troponin I and T).

Moreover, many agglutination test kits for infectious diseases have been made, including mononucleosis, streptococcus infection, staphylococcus infection, toxoplasma infection, trichomonas infection and syphilis.

Such reagents and reagent sets are either based upon detection of the infectious agent itself, or detection of antibodies produced by the body as a reaction to the infectious disease.

A typical medical technique for agglutination assay consists of mixing a sample with one or more agglutination reagents. Binding sites on the agglutination reagent(s) bond to corresponding sites on components of the sample, if present, and this binding results in agglutinates, which are visible clusters of bonded reagent and sample component. Thus, a desired reagent may be mixed with a sample and the presence of agglutinates in the mixture indicates the presence of the corresponding component in the sample. So a commercial latex particle agglutination test on slide it's used (like Toxocell Latex, made by Biokit of Barcelona, Spain).

A typical latex agglutination slide-based test, such as Toxocell Latex, made by Biokit of Barcelona, Spain is described below.

Primary Screening: Serum sample and latex reagent are mixed with a wooden stick on a slide section for approximately 5 minutes. Sample solvent is used as a negative control. After that, the slide is watched under direct and intense light for the presence or absence of agglutination. Results are recorded according to: positive reaction (3+ large aggregates on clear background, 2+ medium-sized aggregates on a slightly cloudy background, 1+ small aggregates on a cloudy background (for assay purposes, aggregates barely visible on milky background may be considered a positive indication) or negative reaction (absence of agglutination: milky uniform aspect).

Titration technique: the sample undergoes two serial dilutions with sample solvent over a single slide and is processed in accordance with the primary screening method described above. However, a titre of a given sample corresponds to the highest serum dilution that still presents a clearly visible agglutination (+1 according to the above scale). Provided that samples are tested in two fold dilutions, the real concentration will be in the range from that of the first and second dilution. With this technique, there is no way to determine the real concentration and in the technique is thus, useful in cases where it is the variation of concentration as opposed to the real concentration, that is of interest.

Although traditional agglutination reactions are, in fact, quantitative in nature, the interpretation of the result is traditionally qualitative.

However, since many of the analytes which may be the subject of such agglutination reactions are desired to be measured quantitatively, other and more complicated methods like ELISA, RIA, immunofiltration or immuno-chromatography methods have been used.

A few patents try to address the problem of quantitative vs. qualitative analysis in the context of agglutinate assays by the application of automatic procedure to a scanned image of the agglutinate assay. PCT International Application WO0005571, describes a device and method for the quantification of agglutination reactions based on a digital image of the agglutination reaction. Although this patent presents examples where samples with different concentrations produce different values in the measured features, no evidence is presented towards the reproducibility of such analysis. In some of the examples the obtained curves of measured features versus concentration have extremely small regions where quantification may be possible. Last but not least, the patent does not study the reproducibility of the process which is mandatory for automatic and general diagnostic systems. In several cases, agglutination patterns include great variations which are not accounted for when using these kinds of systems (see FIG. 2). The method proposed by PCT International Application WO0005571 does not address this problem. Since no preprocessing is applied to the image before feature extraction, great variations in the process can occur due to non uniform illumination, noise, dirt and bubbles, in addition to variations in the sample itself. Further, the procedure to obtain the reaction is completely manual, i.e., a wooden stick is used for the mixing of reagents and distribution thereof over a plate surface. This actually worsens the distribution of the agglutinates, as the particles will be formed erratically on an irreproducible fashion, causing the particles to increase in height. Accordingly, so any results obtained are typically inaccurate.

In U.S. Pat. No. 5,541,417, a similar method is proposed. A digital image of the agglutination reaction is obtained and processed. The quantification is based on a roughness index that captures the pixel local variations. These kinds of texture descriptors are efficient when dealing with uniform textures. However, as noted above, in the general case of agglutination reactions, great variations in the agglutination patterns are expected. As said before, these variations are often related with sample characteristics that can not be inferred a priori. Therefore, the roughness will produce different output values for samples with equal concentrations but different agglutination patterns. In a second embodiment the patent proposes to use a neural network to generalize local intensity variations. Neural networks must be trained using a sufficiently rich training data. This is a limitation in diagnostic systems where reagents may change over time, producing variations in the agglutination patterns. Therefore, every time changes are made to the system the network must be trained and sent to all the users of the system. On the other hand, as mentioned above, agglutinations with similar concentrations may have different agglutination patterns (see FIG. 2) and a neural network based only on a roughness measure will have problems to accurately quantify the sample.

Another example of the application of this technique involves blood group serology, where agglutination is the result of mixing red cells (containing a particular antigen) with a serum containing the corresponding antibody. Blood typing tests are done before a person receives a blood transfusion and to check a pregnant woman's blood type. Human blood is classified, or typed, according to the presence or absence of certain markers (called antigens) on the surface of red blood cells. The most important antigens are blood group antigens (ABO) and the Rh antigen. Therefore, the two most common blood typing tests are the ABO and Rh tests.

With respect to this type of agglutination assay, PCT International Application WO8907255 attempts to solve a normal operation problem with the automatic detectors for hemoagglutination test. In the normal procedure, the way in which the agglutinate deposits over the walls and bottom of the sample cell (or plate depression), make the automatic detection of the agglutination difficult. Normally a small button is formed on the centre of the reaction surface, and other deposits are scattered unevenly across the surface. The method appears to solve those problems only in cases when a positive/negative detection is needed, comparing the absorbance values of the centre and periphery zones of the bottom of the cell (or plate). However the described method cannot be applied to diluted samples, usually found when the analyte concentration is low, and/or the absorbance difference between both zones is low and each absorbance value is close to zero (because the high dispersion of the agglutinates).

Thus, traditional agglutination assays have been carried out only semi quantitatively, and the interpretation of results obtained therefrom are subject to human error inaccuracy and are often not reproducible.

SUMMARY OF THE INVENTION

To overcome some of the disadvantages described above, there is provide a method for acquiring a digital image of an agglutination result comprising performing an agglutination assay on a reaction substrate having a set of dimensions and characteristics which permit a pattern of agglutination in a result of said assay. The image of the result is developed. The image has a colored background which maximizes a signal to noise ratio. Further, the image has been passed through a filter that complements an action of the colored background and enhances the agglutinates in the image while additionally increasing the signal to noise ratio.

In another specific enhancement the pattern is related to a concentration of interest in the sample.

In another specific enhancement the image is acquired using a flatbed scanner.

In another specific enhancement the image is acquired using a camera.

In another specific enhancement the image is acquired using an array of photodetectors.

Another aspect of the invention is a method for analyzing an agglutination assay comprising performing an agglutination assay by mixing a volume of a sample dilution with a corresponding volume of at least one reactive and observing a formation of agglutinates. A negative control is prepared by mixing a second volume of the sample dilution equal to the volume of sample dilution with a second corresponding volume of the reactive. A digital image of the sample dilutions is obtained. The digital image is processed against a calibration curve to generate a quantitative result value representative of a degree of agglutination of the sample and reactive.

In another specific enhancement the method further comprises processing the image by automatically identifying and quantifying the samples present in the digital image of the assay.

More specifically, the method comprises extracting a set of features. A quantification function which maps measured features to the actual concentration of the sample is obtained. A quantitative result for each sample in the assay is extracted.

Yet another aspect of the invention, is a method of extracting a set of features that characterize a set of agglutination results, the method comprising applying a digital or optical filter to extract a component of the image or portion of a spectrum where a signal to noise ratio between agglutinates and background is maximized. A top-hat transform with a spherical structural element is applied to obtain a new image referred as Rd and assign the set of pixels to within each well to a matrix referred as Rdi. The pixels within a well produced by the agglutination reaction are extracted. A mean of the pixels in Rdi is computed. A standard deviation of the pixels in Rdi is computed. At least one other statistical and texture descriptor are computed. An estimated area of the agglutinates is determined.

In another specific enhancement the statistical and textual descriptor is at least one of Media, Absolute Deviation, Kurtosis and moments of co-occurrence Matrices.

Another aspect of the invention is a method for obtaining a quantification function F for a dilution which maps a set of measured features to an actual concentration of the sample, the method comprising making a table with entries: Dilution, Mean and Concentration (UI/ml). A least squares analysis is applied to a region above a point of negative response and below a point of saturation to adjust a parametric function to the table. Safeguard thresholds are obtained for indicating a beginning and an end of a quantification zone and confidence weights. A Th+ value, that defines a set of values of a feature that corresponds to positive agglutinations is obtained.

Another aspect of the invention is a method for extracting a quantitative result for each dilution of a sample based on its agglutination features, a quantification function and a set of dilutions, the method comprising. For each agglutination feature (fi), fi is compared with an obtained Th+ value that defines values of a feature that corresponds to positive agglutinations. If fi>Th+, a dilution is declared as positive. For a last positive dilution (fj), if fj falls within a quantification region, its concentration Q is estimated as: $Q=F(fj)*j$. Th+, fj and Q values are validated if an area measure is above a threshold of a negative control and below saturation. A final result is obtained by determining a weighted average of the validated values.

Another aspect of the invention is a method of evaluating an agglutination assay comprising obtaining a semiquantification table F using a set of labeled patient samples. A set of pattern recognition techniques are applied to determine a set of thresholds which divide each agglutination into an agglutination class with a minimum probability error. A threshold Th+ which divides positive and negative agglutination reactions is obtained. For each patient sample, a semiquantification process is obtained for an evaluation of the agglutination.

More specifically, a semiquantification training table F is obtained using a process comprising for each image in a training sample, processing all reactions with the feature extraction method to obtain a set of agglutination features. A table is made with entries for Given Agglutination Score and Feature.

More specifically, a semiquantitative result for evaluating an agglutination assay is obtained using a method comprising measuring a feature that characterizes the agglutination. A threshold (Th+) is obtained. For each positive reaction, the semiquantification table F is used to obtain an agglutination score.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein:

FIG. 5 shows Table 1, which includes the details of procedures that are discussed herein.

FIG. 6 shows Table 2, which includes the results of each dilution.

FIG. 7 shows Table 3, which includes results for Example 1.

FIG. 8 shows Table 4, which includes results for Example 2.

FIG. 9 shows Table 5, which includes results for Example 2.

FIG. 10 shows Table 6 which includes results obtained with proposed semi-quantification process with the results given by a human expert.

FIG. 11 shows Table 7 which shows a confusion matrix with classification results.

DETAILED DESCRIPTION OF THE INVENTION

Figure 1:
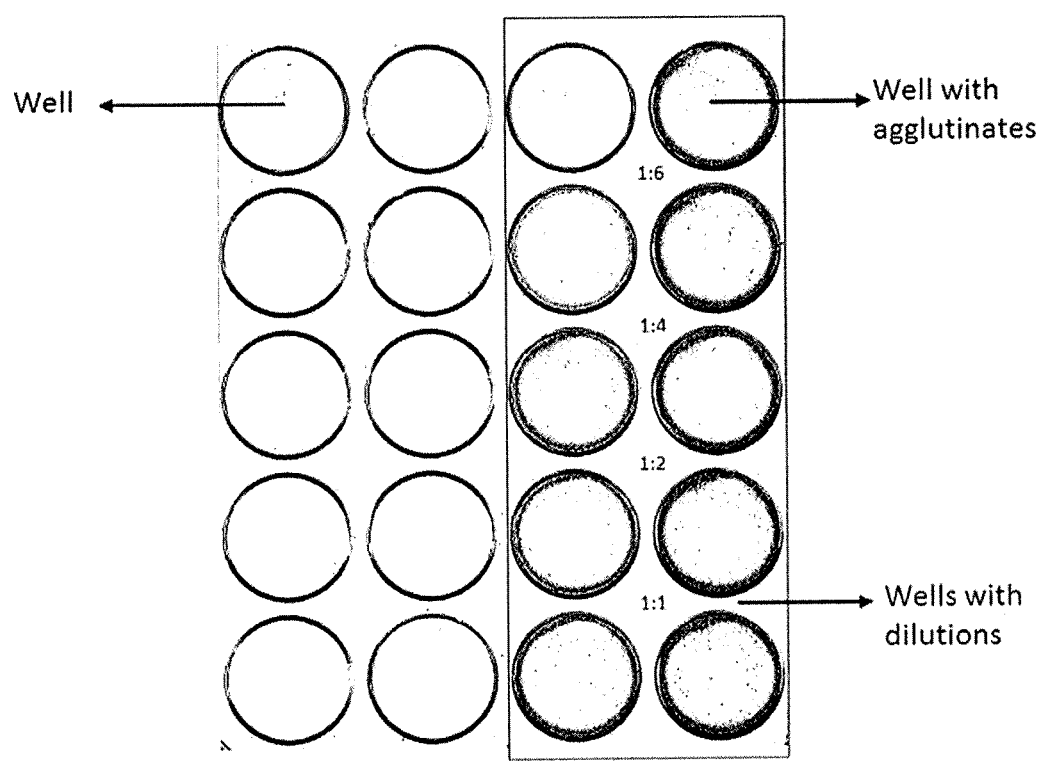
FIG. 1 is a scanned image of the plate used in Example 1. At the upper-left corner is a negative control. From the bottom-right and up is a set of dilutions for a given sample. Starting from a 1:1 dilution 1:2, 1:4, 1:6, etc., dilutions were produced.

Turning in greater detail to the drawings, in which similar reference characters denote similar elements throughout the several views, the attached figures illustrate an apparatus and a preferred process for the automatic quantitative analysis of agglutination assays, which comprises:

a. A digital image acquisition device to acquire a digital image of the agglutination reaction, and b. a set of data processing procedures that process the digital image to automatically obtain a quantitative result of the agglutination reaction.

The image acquisition system can be a desktop flat bed computer scanner, or any other imaging device such as a digital camera, video camera, or any other array of light detectors.

The data processing may be carried out by a set of procedures implemented in a personal computer but other more specific digital systems as custom electronics can be used.

The digital image may have an arbitrary number of channels, directly acquired by the acquisition system or produced with other methods like optical or digital filtering and/or processing.

The assay is performed on any suitable substrate such as a plastic plate. In order to hold each sample in a confined area, the substrate may contain predefined wells of appropriate shape and dimensions. This facilitates the identification of each sample and fixes the height of each sample given the volumes of sample and reagents For example, the surface of the reaction plate may be shaped so that the reaction mixture is enclosed within a distinct region in order to improve reproducibility in quantitative readings. This may be achieved by a circular elevation in a plastic surface, which can be made according to standard production methods, or by the use of a microtitre plate.

The determination of the quantitative result may involve the extraction of a set of features from the digital image. These features characterize the pixel distribution for each sample in the assay and relate them with a quantitative result.

As an example of the use of the invention, the procedure is applied to a commercial latex agglutination kit for quantitative determination of antibodies to a certain protozoan in serum. Other uses of the mentioned technique include any particulate agglutination reaction where a reagent such as latex is used; hematies agglutination; bacterial agglutination and RPRs, wherein carbon particles are used as contrasting media which allows for the observation of the agglutination, in which the aggregates and the media are transparent; etc.

After the acquisition of the image, the proposed software implementation of the present procedure gives a quantitative representation of the analyte concentration which can be stored for later reference.

The quantitative automatic determination of the results for each sample in the assay may involve the following steps:

1. the determination of the areas of the digital image that correspond to each sample agglutination result, 2. the extraction of the set of pixels which represent the agglutination results, 3. the computation of a set of features to determine the quantitative result.

The extraction of the portion of pixel actually belonging to the agglutination can be determined by clustering methods that group neighboring pixels of similar features such as gray level, color, texture, etc. [M. Sonka, V. Hlavac, R. Boyle. "Image Processing, Analysis, and Machine Vision", 1999, Second Edition, ITP Publishing.]. The clusters may be also used for the determination of the quantitative results, for example computing their area, shape, color distribution, number, etc. Alternatively, the agglutination regions can be extracted with methods of mathematical morphology such as opening and closing followed by thresholding [M. Sonka, V. Hlavac, R. Boyle. "Image Processing, Analysis, and Machine Vision", 1999, Second Edition, ITP Publishing].

The image acquisition system will preferably use a controlled and uniform light source and possibly a colored background in order to enhance the differences between the agglutination and the background. Even in the case of the use of a flat bed scanner or other controlled light sources, it is important to calibrate the system. For that end, a predefined calibration object may be used. The calibration object may be used before, or at the same time, of the acquisition of the assay image. In either case, the data processing system will compare the image of the calibration object with a stored reference of it. The relationship between both images can be used to translate the obtained pixel values into a reference coordinate system or to reject the image if the lightning conditions cannot guarantee the reliable extraction of the agglutination results.

The same calibration object, or another, can be used to determine the intrinsic parameters of the acquisition system such as magnification, and other geometrical and color distortions. The use of a calibration object will provide a relationship between pixel image characteristics and real dimensions, positions and colors.

Although the system described uses standard white light, it may also use another type of light and photodetectors intended to extract information in other parts of the spectrum such as the infrared or ultraviolet. The system may also use a set of optical and/or digital filters to enhance some portions of the spectrum.

The data processing procedures of the invention are intended to automatically identify and quantify the samples present in the digital image of the assay. The method includes the following steps:

1. determination of the position of the assay substrate in the image, 2. extraction of the areas of each sample, 3. extraction of the pixels within the previous image that correspond to the agglutination result, 4. extraction of a set of features that characterize the agglutination results, and 5. extraction of a quantitative result for each sample in the assay.

Determination of the Position of the Assay Substrate in the Image

The extracted areas of each sample are examined for regions of known shape, corresponding to the predefined wells, being colored differently from that of the background. The use of well-chosen colored backgrounds facilitates this step (discussed below). Additionally, the geometry of the assay substrate can be used to locate potential positions of samples. To detect wells containing samples, the image is pre-processed with a grey level opening with a spherical structure element and is then thresholded [M. Sonka, V. Hlavac, R. Boyle. "Image Processing, Analysis, and Machine Vision", 1999, Second Edition, ITP Publishing.]. This processing fills the gaps in the sample within the well and increases the contrast between samples and background. Using the known shape of the wells, the results of this step can be further improved with a local shape matching procedure.

The pixels corresponding to the agglutination are extracted applying the top-hat transform with a spherical structural element [M. Sonka, V. Hlavac, R. Boyle. "Image Processing, Analysis, and Machine Vision", 1999, Second Edition, ITP Publishing.]. This process subtracts the background and enhances the agglutinates to obtain an image with enhanced agglutinates. The resulting digital image of top-hat transform is referred to as IMD. The pixels corresponding to the agglutination can be then obtained via thresholding. When performing the opening operation the crests of the obtained texture in the digital image are extracted. This texture is caused by the agglutination and is mainly determined by the appearance of agglutinates. These agglutinates reflect the light projected by the light source and appear as bright spots (crests) in the digital image. Applying the previously mentioned processing agglutinates are successfully extracted while canceling non-uniform background. Without this step, most of the features computed from the agglutination would be distorted by the non-uniform background and will not generalize to other cases.

Extraction of a Set of Features that Characterize the Agglutination Results

For each well containing a sample, a set of features that characterize the agglutination are measured. In some cases the agglutination may consist of large agglutinates with high contrast against the background in other cases the agglutination results in almost uniform textured areas. In the former case, the detection may be accomplished by thresholding techniques followed by the determination of the area, number, etc, of the agglutinates, if only the detection of the agglutination is of interest. For the later case, a set of features that characterize the texture is should be identified for detection and quantification of the sample.

The set of features used for the classification of the texture may be composed of one or more of the following features in addition to others: statistical moments of the agglutination pixels (mean, standard deviation, kurtosis, etc), moments of the co-occurrence matrices, fractal signatures, spectral features such as Fourier spectrum, etc. [M. Sonka, V. Hlavac, R. Boyle. "Image Processing, Analysis, and Machine Vision", 1999, Second Edition, ITP Publishing.].

Agglutination Feature Extraction Using the Top-Hat Transforms

To take into account the inherent variability of the technique, it is preferred that the method must be robust and capable of dealing with outliers and defects caused during the reaction manipulation such as bubbles in the sample, stains, colored threads, etc., and inherent problems of the acquisition technique such as uneven illumination. For that end the method applies a preprocessing step before computing features that eliminates these artifacts. As said before, uneven illumination is cancelled while enhancing the agglutination via mathematical morphology.

The sample image is processed with a top-hat transform (For a detailed explanation of the top-hat transform see [M. Sonka, V. Hlavac, R. Boyle. "Image Processing, Analysis, and Machine Vision", 1999, Second Edition, ITP Publishing.]). This process subtracts the background and enhances the agglutinates. After that a mean is computed over the processes sample image, which is shown to be an effective feature. Since the volume of the well is set in order to obtain a thin layer of sample, the mean is a good estimator for the strength of the agglutination, and in this way can be related to the concentration of the sample.

Bubbles can similarly be detected. Artifacts with colors similar to the ones of the agglutinates may be detected and removed observing their shapes and sizes.

It is desirable to have an optimum total volume in each well for the extracted features to successfully work as a quantitative feature. Ultimately, the total volume is related to several physical and mechanical properties (size of the reagent particles, well diameter, agitation, etc) of the invention. These parameters should be set and adjusted for practicing the remaining steps of the proposed process. Parameters may be set as follows:

In order to enhance the contrast between the agglutinates and the background a colored background may be used. Selection of the background color depends on the wavelength of the reflected light by the agglutinates (for example: latex particles).

The volume and dimensions of the well should be selected based on the next criteria. The well should be rounded enough to avoid overlapping and accumulation of agglutinates on corners (in the case that a rectangular or square well it's used).

The volume of the well it's limited by the access to low volume micropipettes, to avoid the unnecessary excess of costly reactive, and the user ability to handle the small reactives volumes on a small space (avoiding spontaneous mix). Normally a volume between 30 and 120 µL it's advisable.

Also the dimensions of the polystyrene slide are limited by the capture area of the digitalization device, at least 2 well should be on the same image (one for the sample and the other for the negative control)

The diameter should be enough to avoid the spontaneous overlapping of sample and reactive until the operator does it by the use of the stick. Also it may allow the introduction and extraction of the micropipette without problems to easy the work of the operator.

Since the volume of the well is set in order to obtain a thin layer of sample, the height should be choose taking into account all the preferences selected previously.

The parameters used during the assay and the quantification process should guarantee that the reaction to be quantified fall within the region where the measured features and the resulting concentration have a known relationship. That is above the negative reaction zone and below the saturation level.

Special care should be taken with the control of the ambient temperature and the analyte sample concentration. High ambient temperature could increase the agglutination affinity, so it's advisable to run the analysis on a room preferably at 25° C.±5° C.

If the data provided by the patient indicate that the analyte has a high concentration or agglutination affinity (in any case by a previously analysis by the known slide-based test), it's advisable to dilute the sample until the supposed concentration falls between the negative reaction zone and below the saturation level. Others parameters, as the ambient atmospheric pressure have low impact but always it's preferable to try the analysis on a closed room (to avoid dust contamination of the sample). As always it's advisable that the operator it's fully trained.

In this way, the captured image has correlation with the actual concentration of the sample.

If all previous conditions are met, the extracted features, for example the mean, have a strong correlation with the amount of agglutination, and therefore can be used as quantification measures. Quantification using a set of features that characterize the agglutination results With the set of features for each sample, results can be quantified. For quantification, the measured features are compared with the ones of a known standard. That is, the set of features measured are used as argument in a quantification function or table to obtain the quantification result. This quantification result can be evaluated by an ordinary skill in the art using methods known in the art.

To obtain the quantification function or table, samples with known titles are processed with the same technique. Several assays may be used to improve the results such as improved signal relation ratios, that take into account intrinsic technique variability, and make possible, the generalization of the results while avoiding overfitting.

With the obtained results, least squares, robust least squares, or another method [R. Burden, J. Faires. "Numerical Analysis", 2002, Thomson.] may be used to fit a quantification function to the obtained results for the standard sample.

The measure features for the sample are uses as arguments for the quantification function to provide quantification of unknown samples. Several features and quantification functions may be used to improve the results. For that end, techniques of classifier combination may be used. For instance, the quantification of several dilutions can be averaged to improve the results, or consider a combination of a set of features. In both cases confidence weights may also be used. In some cases, it is already known that the method has more sensitivity with some dilutions, etc. These confidence weights can be obtained together with the least square process mentioned above.

This calibration procedure can be performed by the technician at the laboratory since no extra equipment is needed.

Three examples of basic procedures comprising the present automatic quantification process are provided below.

Procedure 1: Feature Extraction

For each well containing an agglutination reaction, the procedure for the extraction of the features characterizes the agglutination result performing the following steps:
1. Apply a digital or optical filter to extract the component of the image or portion of the spectrum where the signal to noise ratio between the agglutinates and background is maximized. For example, an optical filter can be placed between the sample and the sensor to capture the desired portion of the spectrum, or the responses of the multichannel sensor as a color array may be combined to extract the desired component.
2. Apply the top-hat transform.
3. Feature extraction. In this step only pixels within the well are considered, that is, only pixels produced by the agglutination reaction. The set of pixels within the well is herein referred to as Rdi. Compute the mean of the pixels in Rdi: Mean=mean(Rdi).
    a. Computer the standard deviation of the pixels in Rdi: Std=std(Rdi).
    b. Compute other statistical and texture descriptors: Median Absolute Deviation, Kurtosis, moments of the co-occurrence Matrices, etc.
    c. Estimate the area of the agglutinates.
        i. Extract the agglutinates.
        ii. Estimate the area of the agglutinates, Area.

Procedure 2: Obtaining the Quantification Function F.

To obtain the function that maps measured features to the actual concentration of the sample, a set of assays is performed on a standard sample with known concentration. To build the quantification function, a set of predefined dilutions is performed for each sample.
1. For Each Standard Assay (Image):
    a. Process all standard dilutions according to Procedure 1 to obtain the agglutination features of each dilution.
    b. Make a table with entries: Dilution, Feature, Concentration (UI/ml).
2. Apply least squares, robust least squares, or other method to adjust the desired quantification curve F (for example: a piecewise linear function) to the data previously obtained in (1).
3. Obtain safeguard thresholds that indicate the beginning and end of the quantification zone and confidence weights.

Procedure 3: The Quantification Process

For the quantification, all dilutions of the sample are processed. For each dilution, the features that characterize the agglutination are measured. Suppose that dilutions 1, 2, 4, 8, 16, etc. have been done and features: f1, f2, f4, ..., f16, ... etc. have been obtained. Also consider a quantification function F that maps this feature into its concentration (see Procedure 2).
1. If fi>Th+ the dilution is declared as positive. Th+ is obtained together with the function F and defines the values of the feature that correspond to positive agglutinations.
2. Let fj be the last positive dilution.
3. If fj falls within the quantification region, concentration Q can be estimated as:

$$Q=F(fj)*j. \qquad a$$

To validate the measure, the area of the agglutinates may be used. Negative reactions have small agglutinates. Since a negative control is used, samples can be evaluated considering the area differences. Big differences indicate a positive result. This must be done since the features tend to saturate at high concentrations.

To make a more robust estimation, the average of all dilutions falling within the quantification zone is computed. They can be determined from the last positive dilution using suitable safeguard threshold obtained together with the function F.

EXAMPLES

Example 1

The following example was carried out by realizing a Toxoplasmosis agglutination reaction.

Sample Requirements for the Toxoplasmosis Test:

Human serum is collected by centrifugation from clotted human blood, obtained from vein puncture. Preservatives agents should be avoided. If the test is not carried out on the same day, the serum should be stored at 4° C. for a maximum of 48 hrs; for longer periods, it is advisable to freeze the sample.

The reaction may be performed over transparent polystyrene slides, with reaction areas delimited by ledges of the same material defining a circle.

Materials:

Automatic pipettes of 30 and 60 µL.
Disposable tips.
Orbital shaker (speed between 80 to 90 rpm).
Thermometer for measuring from 32.00 to 122.00° F. (able to allow the measure of tents of degree).
Sample Solvent: 8.5 g/l NaCl, 1 g/l BSA (bovine seroalbumine), 1 g/l sodium azide, 1 liter $H_2O$ sqf.
Chronometer.

Latex Reagent

The dilution of a latex reagent should be adjusted previously in accordance with World Health Organization standard serum. This is accomplished by applying standard slide technique, so that the last dilution in which a positive agglutination is detected, corresponds to a concentration of 10 IU/ml (international units by ml of serum).

Sample Preparation:

The sample should be thawed and allowed to reach room temperature, before use. Before performing a set of determinations, latex reagent, controls and solvent should reach a room temperature. The assay should be carried out at a temperature between 68.00 to 86.00° F. The latex reagent should be shaken gently before use (avoiding foaming production).

Figure 2:
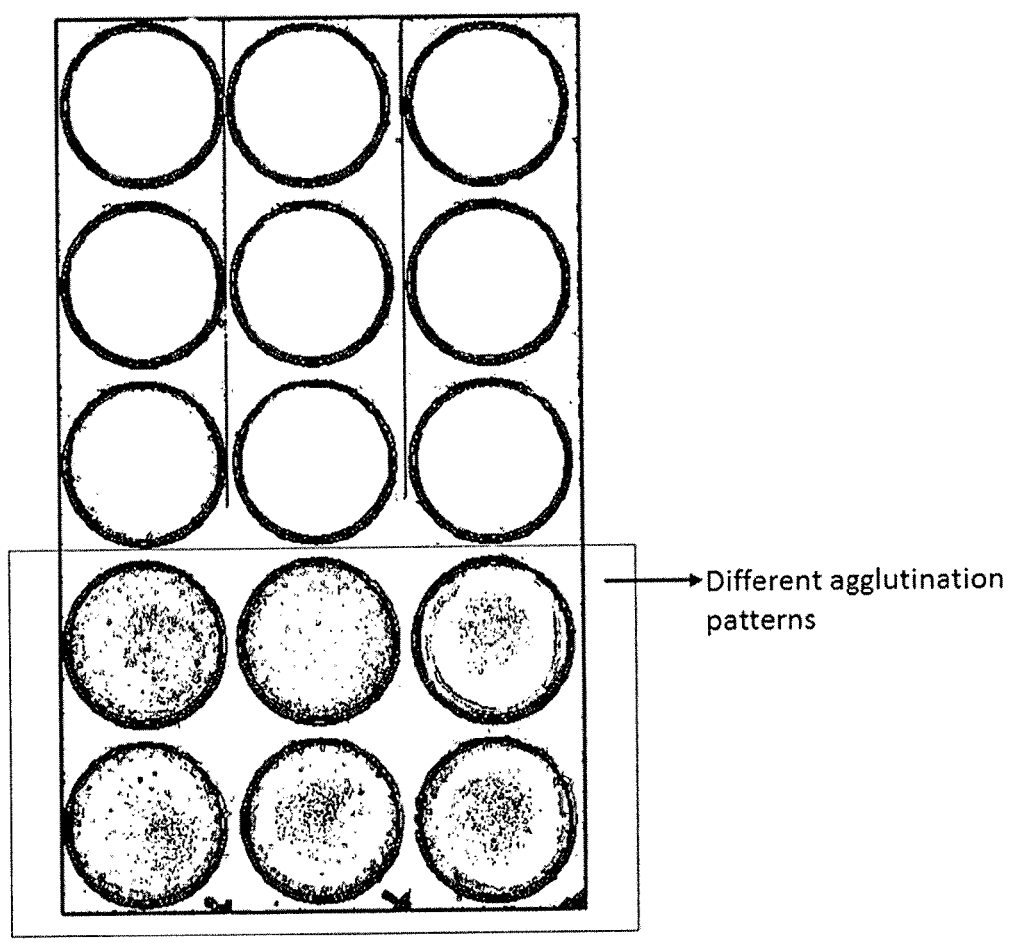
FIG. 2. Shows agglutination results for three samples with almost equal concentrations but different agglutination patterns. From bottom to top 1:1, 1:2, 1:4, 1:8, and 1:16 dilutions are shown.

Primary Screening:
1. Place a previously determined volume A of serum by means of an automatic pipette on one end of the slide hollows.
2. Add a previously determined volume B of latex reagent on the opposite end.
3. Mix both drops with a stirrer, covering the whole surface, allowing the liquid to reach the border of the cavity.
4. Place a previously determined volume A of the sample solvent and mix it with a previously determined volume B of latex reagent on the number 20 section of the slide. It will be use as negative control (FIG. 2).
5. Rotate the slide at 80 rpm for 5 minutes.
6. Obtain the digital image with the associated software against a previously determined dark background, whose color it is selected to increase the definition of the edges of the aggregates.
7. If the results are positive, a titration should be done to obtain the analyte serum concentration.

Titration:

Sample dilutions should be done over the same slide as follows:
1. Add a volume A of sample diluent on each slide section
2. Place a volume A of the sample on section 1.
3. Mix it with the solvent previously placed.
4. Using the same pipette take in and release serum and diluents until they are mixed well (e.g. a 50% dilution)
5. Take a volume A of that dilution and transfer it to section 2. Repeat the stages I to IV.
6. On the last dilution take a volume A and discard them.
7. Obtain the digital image with the associated software against a previously determined dark background, whose color it is selected to increase the definition of the edges of the aggregates.
8. Process the digital image with the procedures 1 to 3 proposed below.

Procedure 1: Feature Extraction Process

For each well containing an agglutination reaction the procedure for the extraction of the features characterizes the agglutination result performing the following steps:
1. Apply the top-hat transform with a spherical structural element to obtain a new image which will be referred as Rd.
2. Feature extraction. In this step, only pixels within the well are considered, that is, only pixels produced by the agglutination reaction. This set of pixels is herein referred to as Rdi.
   a. Compute the mean of the pixels in Rdi: Mean=mean(Rdi).
   b. Computer the standard deviation of the pixels in Rdi: Std=std(Rdi),
   c. Compute other statistical and texture descriptors: Median Absolute Deviation, Kurtosis, moments of the co-occurrence Matrices, etc.
   d. Estimate the area of the agglutinates by extracting the agglutinates using a thresholding method, and estimating the area of the agglutinates(Area=sum(A)).

Procedure 2: Obtaining the Quantification Function F.

Here, focus is on the mean feature and a quantification table is computed that uses the mean to obtain an automatic measure of the concentration of the sample.
1. For each standard assay (image):
   a. Process all standard dilutions with Procedure 1 to obtain the agglutination features of each dilution.
   b. Make a table with entries: Dilution, Mean, Concentration (UI/ml).
2. Apply least squares to adjust a piecewise linear function to the previously obtained table. The fitting is applied in the region above negative response and below saturation.
3. Obtain safeguard thresholds that indicate the beginning an end of the quantification zone and confidence weights.

Procedure 3: The Quantification Process (Using the Mean)

For the quantification, all dilutions of the sample are processed. For each dilution, the mean that characterizes the agglutination is measured. Suppose dilutions 1, 2, 4, 8, 16, etc. have been done and a mean: m1, m2, m4, . . . , m16, . . . etc. is obtained. Also consider a function F that maps the mean values according to their respective concentrations. (see Procedure 2).
1. If mi>Th+ the dilution is declared as positive. Th+ is obtained together with the function F and defines the values of the feature that correspond to positive agglutinations.
2. Let mj be the last positive dilution.
3. If mj falls within the quantification region, its concentration Q can be estimated as:

$$Q=F(mj)*j. \quad\quad a$$

To validate the measure, the area of the agglutinates is used. Negative reactions have small agglutinates. Since a negative control is used samples can be evaluated considering the area differences. Large differences indicate a positive result. This must be done since the features tend to saturate at high concentrations.

To make a more robust estimation, the average of all dilutions falling within the quantification zone is computed. They can be determined from the last positive dilution and using suitable safeguard threshold obtained together with the function F.

Calibration of the System

In these examples, the previously determined volume A corresponds but it is not limited to 60 µL and the previously determined volume B corresponds but it's not limited to 30 µL.

First, the results for the analysis of a set of standard samples with known titles (IU/ml) are shown. The corresponding digital images are acquired using the proposed method. The acquired digital image is processed with Procedure 2 to obtain the quantification function F. The details of each procedure are displayed in Table 1, contained in FIG. 5.

In FIG. 1 one of the scanned images is shown and in the results of each dilution are shown in Table 2, contained in FIG. 6.

In each case: the image number (I, II, III . . . VII), the known IU/ml (4, 6, 8, . . . 24) is shown and the mean value according to Procedure 1 is obtained.

Figure 3:
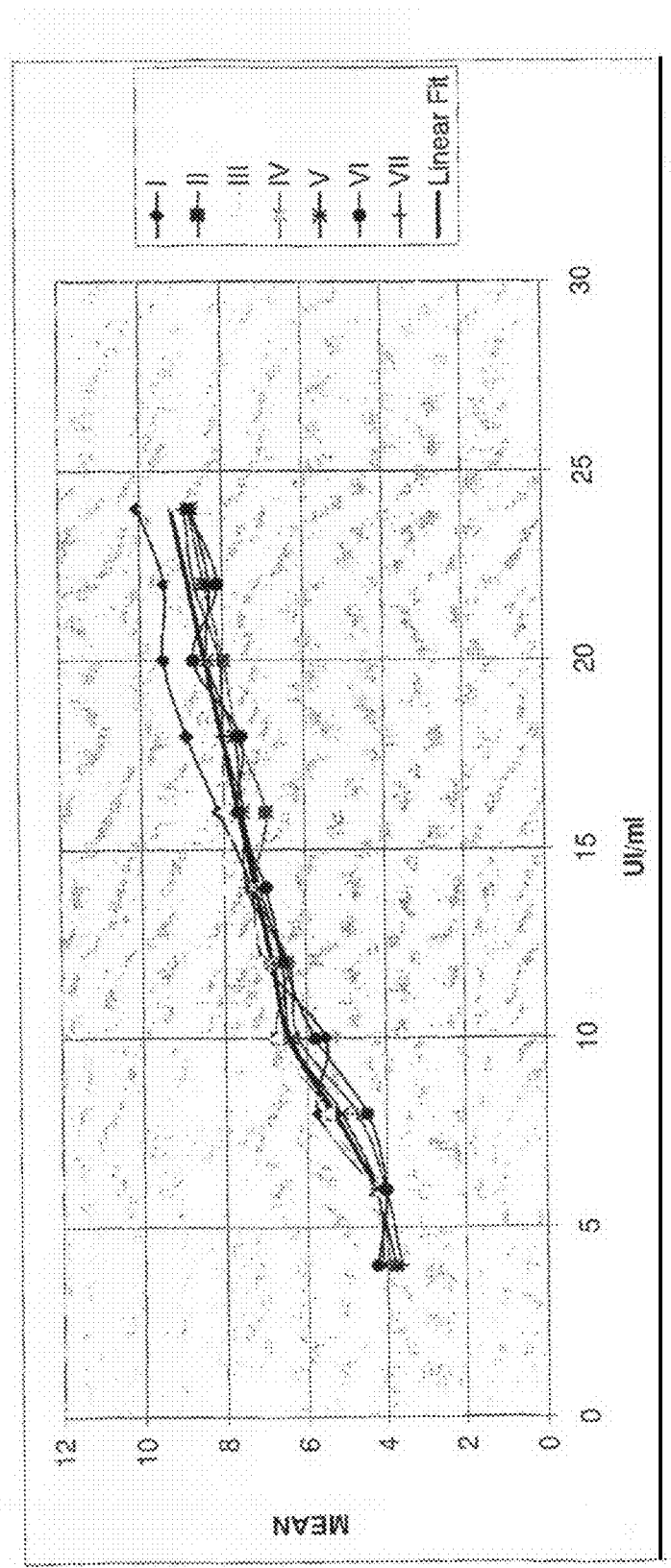
FIG. 3 shows the results for a set of images of standard (samples) and a piecewise linear fit to this data for quantification.

FIG. 3 contains results for all the images with the samples from Table 1 and the calibration curve F, obtained after fitting a pair of lines to the ranges [6, 10] and [10, 24] using Procedure 2.

Examples 1-3, tables for each of which are contained in FIGS. 7-9, include the results of the analysis of samples with unknown IU/ml which are compared with the traditional, manual, technique for reference. With the traditional manual technique, there is no way to find the real concentration, because the normal proceeding takes as the concentration of the analyte, the value of the last dilution with positive agglutination. Actually the real value will be between the last positive and the next two-fold dilution, so it is impossible to obtain a real value by application of the traditional technique. The proposed method is able to produce more fine and accurate results.

Bach of the tables corresponding to Examples 1-3 contains the following information with respect to each well: the dilution, the IU/ml obtained by the agglutination plate method (Ref: traditional technique), the computed mean feature according to Procedure 1 (Mean), the IU/ml for each dilution, the estimated IU/ml using each dilution (multiplying by the dilution) and the estimated IU/ml using all the valid results in third column using Procedure 3. Results are not shown for obtained value that fell outside of the specified linear zones, The quantization was made using the mean feature together with the piecewise linear function of FIG. 3.

For each example, the estimated IU/ml obtained by this method is greater or equal to the supposed known sample value.

Example 2

Example 2 was carried out by realizing a Hemoagglutination reaction.

In this example the application of the proposed method for the semiquantification of hemoagglutination reactions for blood typing is shown.

The traditional technique of hemoagglutination is basically quantitative. However, it is also useful for the hematologist to have a measure of the score of agglutination. The agglutination reactions are classified into five classes: negative, and four positive scores (1 to 4 crosses) depending on the agglutination strength.

Sample Requirements for the Hemoagglutination Test:

Blood collected with or without anticoagulant may be used. Tests are preferably carried out as soon as possible after collection. Samples are preferably stored at 2-8° C. to account for possible delays in conducting the tests. Blood obtained by finger puncture may be tested directly by the slide method, but to avoid clotting, blood collected in this manner should be mixed with the reagent quickly.

The temperature for carrying out the blood grouping reaction is preferably 25° C.±5° C. and the tests are preferably not carried out at 37° C. The reaction may be performed over transparent polystyrene slides, with reaction areas preferably delimited by ledges of the same material defining a circle.

Materials:
Orbital shaker (speed between 80 to 90 rpm).
Thermometer-Chronometer
Transparent polystyrene slides
Reagents:
1. Monoclonal agglutinating sera for the determination of Human blood groups
2. Normal Saline
Procedure:
1. Prepare approximately 5-10% suspension of RBCs (Red Blood Cells) in normal saline.
2. Add one drop of corresponding reagents (AntiB, AntiA, AntiAB, A for reverse grouping, B for reverse grouping, and AntiD) to the each respective well.
3. Add one drop of the above cell suspension (AntiB, AntiA, AntiAB and AntiD) or serum (A for reverse grouping and B for reverse grouping).
4. With separate applicator sticks, mix each cell reagent mixture well.
5. Rotate the slide at 80 rpm for 2 minutes.
6. Obtain the digital image with the associated software against a previously determined white background.

Once a digital image is obtained, the extraction process described in the above examples is applied. Reactions are classified as positive or negative based on the number and area of the agglutinates. Positive reactions may be subsequently classified into four subclasses depending on the agglutination strength, which in turns depends on the number and area of agglutinates. Usually the technicians define four classes, identified with crosses with one cross for the weakest agglutination and four crosses for strongest agglutinations. In some cases a plus/negative may be used to identify border line agglutinations. With the same methodology here describe the classification can be performed to identify other number of classes. The quantization process is based on the mean color of the agglutinates (other features can be used alone or in combination in order to improve the classification results). Accordingly, a semiquantification result for the hemoagglutination reaction may obtained.

An Exemplary Embodiment of the Process Used to Obtain the Semiquantification Table F In an exemplary embodiment, focus is placed on the mean of the agglutinates feature and computing a quantification table that is used to obtain an automatic measure of the score of agglutination of the sample. The following quantification table is obtained using set of samples quantified by an ordinary skill in the art.

1. For each image in the training sample:
All reactions are processed with the disclosed extraction method to determine the agglutination characteristics.
A table containing entries for the following properties is created: Given Agglutination Score, Feature.
2. Pattern recognition techniques are applied to find the thresholds which divide each agglutination class with minimum probability error. In this step the threshold Th+ which distinguishes positive and negative reactions is obtained.

Exemplary Semiquantification Process

For each reaction, the feature that characterizes the agglutination is obtained.

1. If mi>Th+ the dilution is deemed as positive or else the reaction is deemed negative. Th+ is obtained together with the Table F and defines the values of the feature that correspond to positive agglutinations.
2. For each positive reaction, the quantification table, Table F is used to obtain an agglutination score: AS=F(mj).

Figure 4:
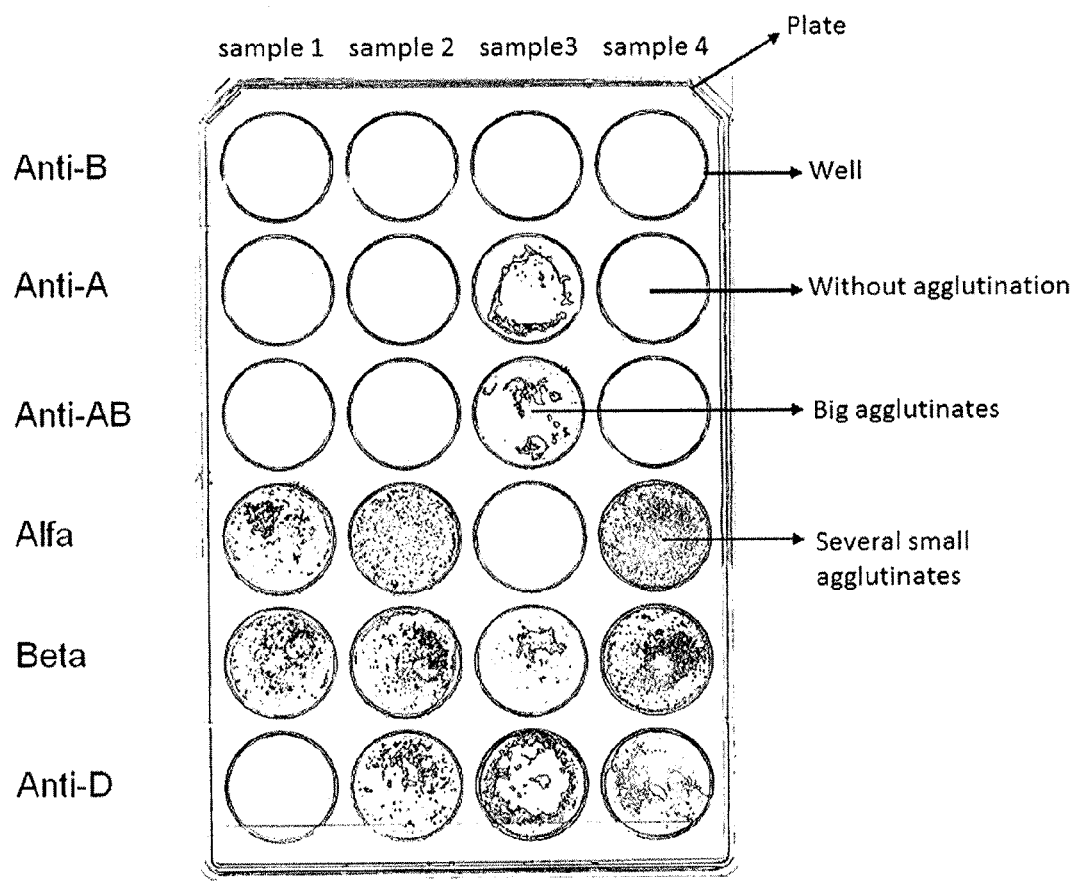
FIG. 4 shows a digital image with the agglutination reactions, containing four blood typing tests.

In FIG. 4, a digital image of agglutination reactions is shown, in the context of four blood typing tests. Each column of wells contains a different sample. Each row contains a different reagent: row 1-anti-B, row 2-anti-A, row 3-anti-AB, row 4-alpha, row 5-beta, row 6-anti-D. As can be seen, the pattern of agglutination has strong variations.

Table 6, contained in FIG. 10, provides results obtained together with the quantification given by an ordinary skill in the art. Cells shown in brackets correspond to classification errors. These errors correspond to score. The blood group obtained by the presently disclosed system reflects no error.

The disclosed method was tested against 500 reactions and comprised only 1% false negatives. The false negatives were all alpha or beta reactions and therefore, it is reasonable to conclude that said false negatives did not affect the typing result. Accordingly, 0% error in group typing was obtained.

For verification, in Table 7, contained in FIG. 11, a confusion matrix for the score classification is shown.

As can be seen most of the samples are classified in the correct class. Most of the samples which are not classified in the correct one, shift to the neighboring classes as expected.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. A method for analyzing a digital image of an agglutination assay, the method comprising:
    a) performing an agglutination assay by mixing a volume of a sample dilution with a corresponding volume of at least one reactive and observing a formation of agglutinates;
    b) preparing a negative control by mixing a second volume of the sample dilution equal to the volume of sample dilution of (a) with a second corresponding volume of the reactive of (a);
    c) obtaining a digital image of the sample dilutions processed in (a) and (b); and
    d) processing said digital image against a calibration curve, and thereby generating a quantitative result value representative of a degree of agglutination of the sample and reactive.

2. The method of claim 1 further comprising
    e) processing the image by automatically identifying and quantifying the samples present in the digital image of the assay.

3. The method of claim 2 further comprising:
    f) extracting a set of features;
    g) obtaining a quantification function which maps measured features to the actual concentration of the sample; and
    h) extracting a quantitative result for each sample in the assay.

4. A method of extracting a set of features that characterize a set of agglutination results, the method comprising:
    a) applying a digital or optical filter to extract a component of an image or a portion of a spectrum where a signal to noise ratio between agglutinates and a background is maximized;
    b) applying a top-hat transform with a spherical structural element, thus obtaining a new image referred to as Rd and assigning a set of pixels to within each well to a matrix referred as Rdi;
    c) extracting pixels within a well produced by the agglutination reaction;
    d) computing a mean of the extracted pixels in Rdi;
    e) computing a standard deviation of the extracted pixels in Rdi;
    f) computing at least one other statistical and texture descriptor; and
    g) determining an estimated area of the agglutinates.

5. The method of claim 4, wherein the statistical and textual descriptor is at least one of Media, Absolute Deviation, Kurtosis and moments of co-occurrence Matrices.

6. The method of claim 4, further comprising: obtaining a semiquantification training table F using a process comprising:
    h) for each image in a training sample, processing all reactions with the feature extraction method to obtain a set of agglutination features; and
    i) making a table with entries for Given Agglutination Score and Feature.

7. A method performed by a computer comprising a central processing unit (CPU) and a memory, the method being for obtaining a quantification function F for a dilution which maps a set of measured features to an actual concentration of a sample, the method comprising:
    a) making a table with entries comprising: Dilution, Mean and Concentration (UI/ml);
    b) applying a least squares analysis to a region above a point of negative response and below a point of saturation to adjust a parametric function to the table;
    c) obtaining performed by the CPU, safeguard thresholds for indicating a beginning and an end of a quantification zone and confidence weights; and
    d) obtaining a Th+ value, that defines a set of values of a feature that corresponds to positive agglutinations.

8. A method performed by a computer comprising a central processing unit (CPU) and a memory, the method being for extracting a quantitative result for each dilution of a sample based on its agglutination features, a quantification function and a set of dilutions, the method comprising:
    a) obtaining the quantification function F for a dilution which maps a set of measured features to an actual concentration of the sample, comprising:
        i) making a table with entries comprising: Dilution, Mean and Concentration (UI/ml),
        ii) applying a least squares analysis to a region above a point of negative response and below a point of saturation to adjust a parametric function to the table;
        iii) obtaining performed by the CPU, safeguard thresholds for indicating a beginning and an end of a quantification zone and confidence weights; and
        iv) obtaining a Th+ value, that defines a set of values of a feature that corresponds to positive agglutinations;
    b) for each agglutination feature fi for a dilution i, comparing fi with an obtained Th+ value that defines values of a feature that corresponds to positive agglutinations;
    c) if fi>Th+, declaring a dilution as positive;
    d) for a last positive dilution fj, if fj falls within a quantification region, estimating its concentration Q as: Q=F(fj)*j, wherein F(fj) is the quantification function F from (a) evaluated at value fj and j is the corresponding dilution of the sample;
    e) validating Th+, fj and Q values if Th+, fj and Q values are above a threshold of a negative control and below saturation; and
    f) obtaining a final result by determining a weighted average of the validated values.

9. A method performed by a computer comprising a central processing unit (CPU) and a memory, the method being of evaluating an agglutination assay, the method comprising:
    a) obtaining a semiquantification table F using a set of labeled patient samples;
    b) applying a set of pattern recognition techniques to determine a set of thresholds which divide each agglutination into an agglutination class with a minimum probability error;
    c) obtaining performed by the CPU, a threshold Th+ which divides positive and negative agglutination reactions; and
    d) for each patient sample, applying a semiquantification process for an evaluation of the agglutination.

10. The method of claim 9, further comprising: obtaining a semiquantitative result for evaluating the agglutination assay using a process comprising:
    e) measuring a feature that characterizes the agglutination;
    f) obtaining a threshold (Th+); and
    g) for each positive reaction, using the semiquantification table F to obtain an agglutination score.

\* \* \* \* \*